(12) United States Patent
Paques et al.

(10) Patent No.: US 8,808,242 B2
(45) Date of Patent: Aug. 19, 2014

(54) APPARATUS FOR INJECTION INTO AN EYE

(75) Inventors: Michel Paques, Neuilly-sur-Seine (FR); Pierre Roy, Paris (FR)

(73) Assignee: Fovea Pharmaceuticals, Paris (FR)

( * ) Notice: Subject to any disclaimer, the term of this patent is extended or adjusted under 35 U.S.C. 154(b) by 0 days.

(21) Appl. No.: 13/881,799

(22) PCT Filed: Nov. 2, 2011

(86) PCT No.: PCT/EP2011/069255
§ 371 (c)(1),
(2), (4) Date: Apr. 26, 2013

(87) PCT Pub. No.: WO2012/059517
PCT Pub. Date: May 10, 2012

(65) Prior Publication Data
US 2013/0211335 A1    Aug. 15, 2013

(30) Foreign Application Priority Data
Nov. 2, 2010 (EP) .................................. 10306197

(51) Int. Cl.
*A61M 5/00* (2006.01)
(52) U.S. Cl.
USPC ........................................................ 604/117
(58) Field of Classification Search
USPC .................................. 604/116, 117, 187, 294
See application file for complete search history.

(56) References Cited

U.S. PATENT DOCUMENTS

| 7,678,078 B1 | 3/2010 | Peyman et al. |
| 8,460,242 B2 * | 6/2013 | Paques et al. ................. 604/116 |
| 2005/0288697 A1* | 12/2005 | Tei et al. ........................ 606/166 |
| 2006/0271025 A1* | 11/2006 | Jones et al. ........................ 606/4 |
| 2010/0010452 A1* | 1/2010 | Paques et al. .................. 604/192 |
| 2010/0030150 A1* | 2/2010 | Paques et al. .................. 604/116 |
| 2010/0152646 A1* | 6/2010 | Girijavallabhan et al. ...... 604/22 |
| 2010/0241102 A1 | 9/2010 | Ma |

FOREIGN PATENT DOCUMENTS

| EP | 0437953 | 7/1991 |
| EP | 1310222 | 5/2003 |
| WO | 2008/084063 | 7/2008 |
| WO | 2008/084064 | 7/2008 |

OTHER PUBLICATIONS

International Preliminary Report on Patentability for Int. App. No. PCT/EP2011/069255, mailed May 16, 2013.
International Search Report and Written Opinion for Int. App. No. PCT/EP2011/069255, completed Dec. 7, 2011.

* cited by examiner

*Primary Examiner* — Aarti B Berdichevsky
(74) *Attorney, Agent, or Firm* — McDonnell Boehnen Hulbert & Berghoff LLP

(57) ABSTRACT

The invention relates to an apparatus for injection into an eye comprising of a means for displacing a conjunctival layer of the eye over an underlying scleral layer of the eye so as to form a fold in the conjunctival layer, and means for guiding a needle through the conjunctival layer once the fold has been formed.

14 Claims, 7 Drawing Sheets

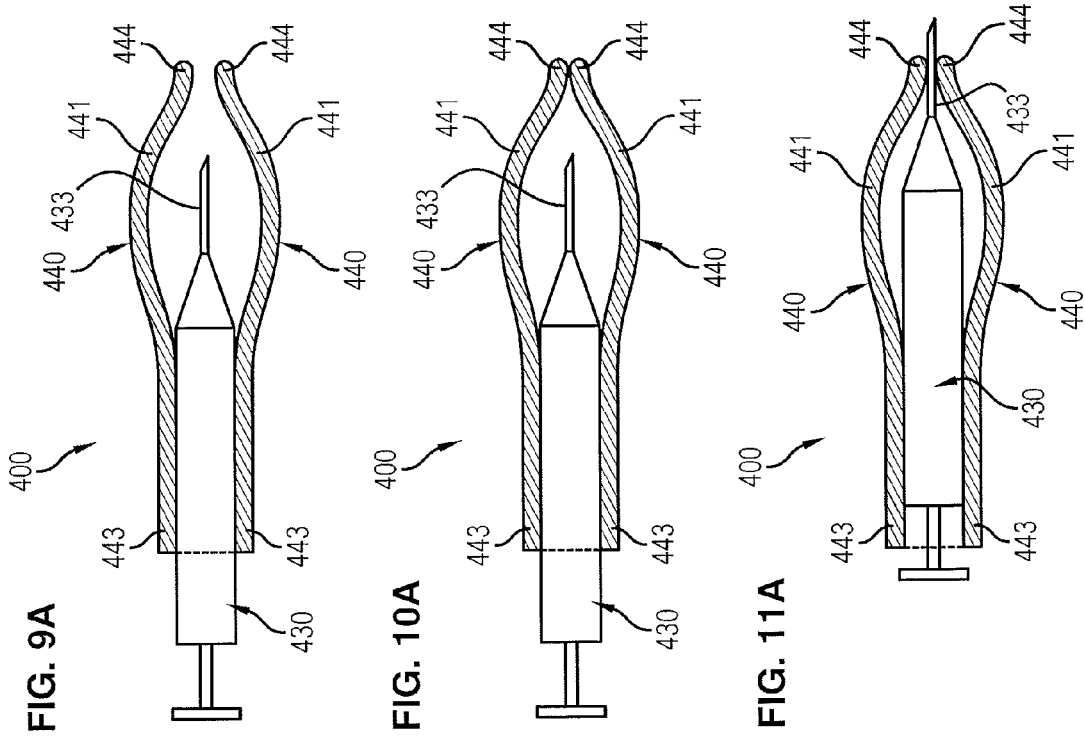

APPARATUS FOR INJECTION INTO AN EYE

CROSS REFERENCE TO RELATED APPLICATIONS

The present application is a U.S. National Phase Application pursuant to 35 U.S.C. §371 of International Application No. PCT/EP2011/069255 filed Nov. 2, 2011, which claims priority to European Patent Application No. 10306197.4 filed Nov. 2, 2010. The entire disclosure contents of these applications are herewith incorporated by reference into the present application.

FIELD OF THE INVENTION

The invention relates to an apparatus for injection into an eye, and in particular for intraocular or subconjunctival or subtenon injection.

Intraocular injection is commonly used in ophthalmology for delivering therapeutics or agents (e.g. drugs of interest) to the posterior segment of the eye, especially when it is useful to deliver high concentrations of drugs. Such an operation is used in particular for injecting compositions comprising for example corticosteroids or neovascularization inhibitors in the vitreous body of the eye, in order to treat diseases affecting retina or choroid, or ciliary body or lens.

Intraocular injection procedure generally consists in:
moving apart the eyelids with an eyelids refractor,
locating an injection area on the eye using a compass,
introducing the needle into the eye at the level of the injection area, and
injecting a composition via the needle, and
removing the needle while pressing the superficial layers of the eye in the injection area in order to limit the risk of leakage of the injected substance.

Such a procedure requires high technical skills and lots of practice. For this reason, many non-qualified operators are not able to carry out such operations.

In particular, the injection area must be precisely defined. In order to avoid damaging structures located in front of the vitreous body (such as cornea, iris and lens crystalline) and structures located at the rear of the vitreous body (such as retina), the needle is generally introduced at a given distance, usually around 3 to 4 mm, from the limbus zone, which is a transition zone extending between the cornea and the sclera.

The depth of penetration of the needle into the eye must also be carefully controlled.

Additionally, precautions must be taken in order to limit risks of complications due to perforation of eye tissues.

In particular, perforation of the tissues can cause leakage of the injected composition out of the eye though the orifice created by the needle. This phenomenon prevents the operator from controlling the amount of active compound that has been actually introduced into the eye.

Moreover, perforation of the tissues can also favour penetration of germs into the eye, causing ocular infections.

Document WO 2008/084064 discloses an apparatus for intraocular injection comprising a plate adapted for being brought into contact with an eye, guiding means for guiding a needle into the interior of the eye, and means for displacing a superficial layer of the eye (called "conjunctiva") over an underlying layer of the eye (called "sclera") as the plate is brought into contact with the eye before the needle is guided into the interior of the eye. The means for displacing the superficial layer over the underlying layer comprises a resilient member which can be bent when urged against the superficial layer so as to apply a tangential force on the superficial layer.

By displacing a superficial layer of the eye over an underlying layer of the eye, the layers are shifted one relative to the other, so that the needle pierces the layers in two different zones. When the apparatus is removed from the eye, the superficial layer comes back to its initial position, thereby closing the orifice created by the needle in the underlying layer. Therefore, the composition which has been injected into the eye is prevented from leaking out of the eye. Moreover, this also avoids penetration of germs into the eye.

However, with this apparatus, there is a risk that the entire eye globe moves under the effect of the tangential force applied by the resilient member.

Moreover, experiments have shown that the natural elasticity of the conjunctival layer frequently prevent significant displacement of the conjunctival layer relative to the scleral layer at the site of injection.

In such cases, it may happen that the apparatus does not cause sufficient shifting of the superficial layer relative to the underlying layer prior to injection.

Moreover, in certain cases, it would be desirable to make a subconjunctival injection for delivering the composition just between the conjunctiva and the sclera, or subtenon injection for delivery of composition just between the tenon and the sclera. However, the apparatus disclosed in document WO 2008/084064 does not allow injecting a composition between the superficial layer and the underlying layer.

SUMMARY

It is an object of the invention to ensure sufficient shifting of the superficial layer over the underlying layer in the injection area.

This problem is solved according to the invention thanks to an apparatus for injection into an eye according to claim 1. The apparatus comprises:
means for displacing a conjunctival layer of the eye over an underlying scleral layer of the eye so as to form a fold in the conjunctival layer, and
means for guiding a needle through the conjunctival layer once the fold has been formed.

The forces used to form a fold in the conjunctival layer allow a displacement of the conjunctival layer over the underlying scleral layer without applying a tangential force on the entire globe of the eye and without loss of displacement amplitude due to elasticity of the conjunctival layer. Therefore, the globe of the eye is prevented from moving during intervention and sufficient shifting of the conjunctival layer can be obtained.

Moreover, with such an apparatus, it is possible to inject a composition within the fold, i.e. between the conjunctival layer and the scleral layer, if required.

Other advantageous features are recited in dependant claims. In particular, the apparatus can have the following features:
the means for displacing the conjunctival layer comprise two mobile legs adapted to be brought closer one to the other for pinching the conjunctival layer so as to form the fold,
one of the mobile legs comprises a hole or an encroachment for allowing the needle to pass through the mobile leg,
the apparatus comprises a plate for being brought into contact with the eye, the mobile legs are extending from the plate, the mobile legs being caused to flex relative to the plate when the plate is brought close to the eye, the plate comprises a cut-out having an edge adapted to be positioned along a limbus delimiting a cornea and a sclera of the eye so as to adjust a position of the guiding means relative to the limbus, each mobile leg is arranged so as to form an angle comprised between 10° and 80° relative to a bearing surface of the plate, the means for displacing a conjunctival layer comprise means for engaging the conjunctival layer, the means for engaging the conjunctival layer comprises a relief adapted for biting into the conjunctival layer, the means for guiding the needle comprises a hollow body adapted for receiving a barrel of a syringe, the means for guiding the needle are arranged so that the needle penetrates through the conjunctival layer at the foot of the fold, the means for guiding the needle are arranged so that the needle penetrates through the conjunctival layer at the fold for injection between the conjunctival layer and the scleral layer, the means for guiding the needle are arranged so that the needle penetrates through the conjunctival layer with an angle comprised between 0° and 20°, preferably between 10° and 20°, relative to a radial direction of the eye at a penetration point, the means for guiding the needle are arranged so that the needle penetrates through the conjunctival layer according to a direction parallel to a tangential direction of the eye at the fold, the apparatus comprises releasable locking means for preventing accidental movement of the needle relative to the guiding means before the fold is formed, the apparatus comprises means for releasing the needle once the fold is formed.

BRIEF DESCRIPTION OF THE DRAWINGS

The invention will be described with reference to the drawings, in which:

FIGS. 9 to 11 illustrate different steps of a method for performing subconjunctival or subtenon injection using the apparatus of FIG. 8.

DETAILED DESCRIPTION

Figure 1A:
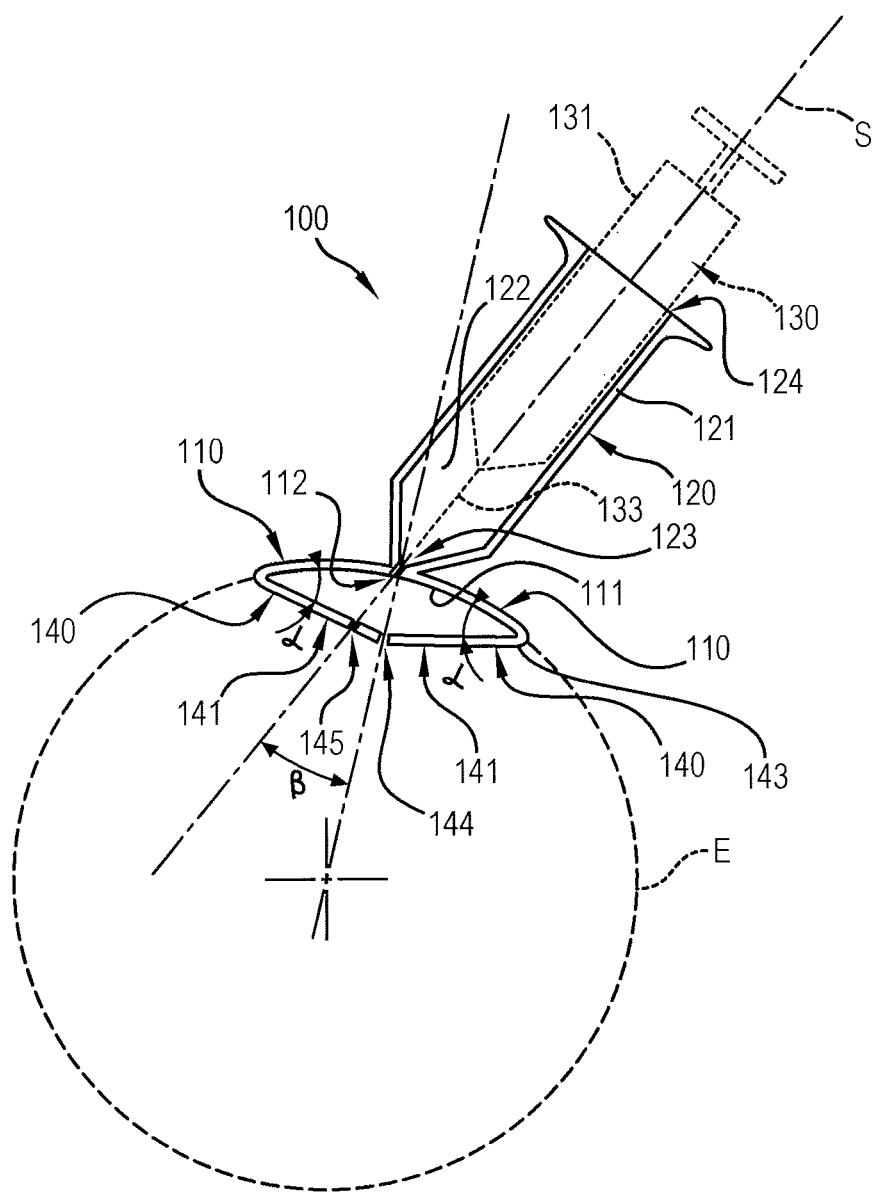
FIGS. 1A and 1B are respectively schematic front view and bottom view of an apparatus for intraocular injection according to a first embodiment of the invention.
Figure 1B:
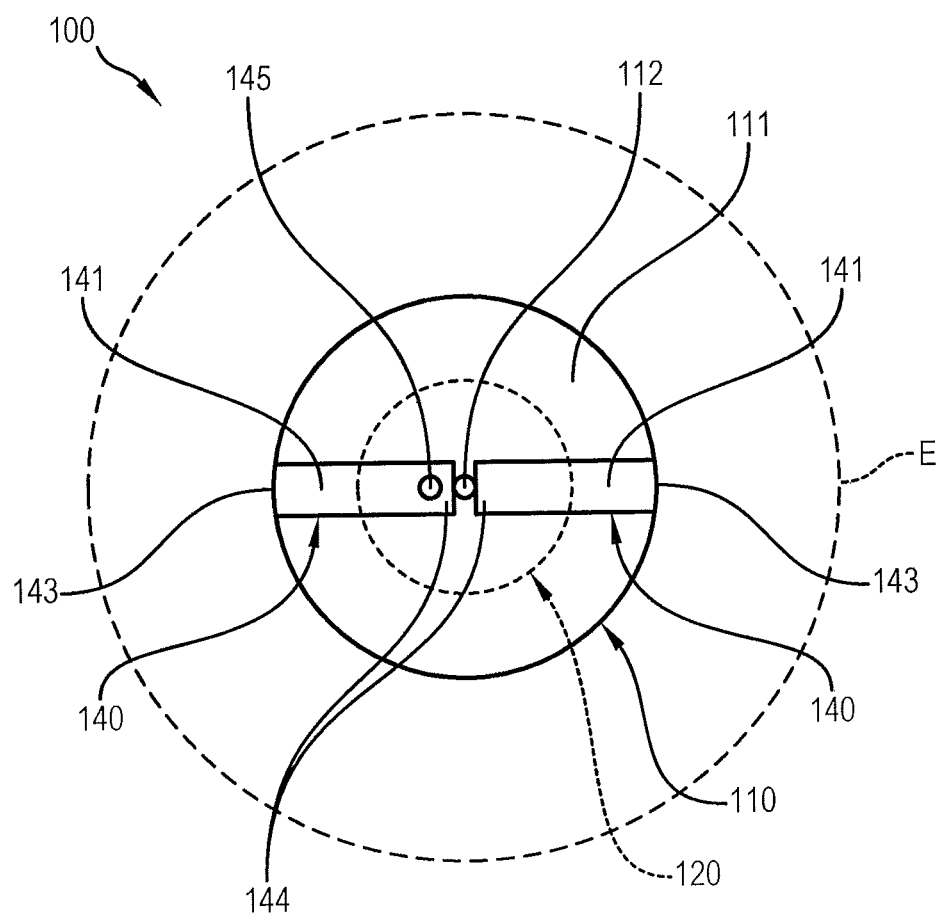

FIGS. 1A and 1B illustrate an apparatus 100 for intraocular injection according to a first embodiment of the invention.

The apparatus 100 comprises a plate 110 adapted for being brought into contact with an eye, a support 120 for receiving a syringe, optionally a syringe 130, and two resilient members 140 for displacing a conjunctival layer of the eye over an underlying scleral layer of the eye.

The plate 110 has an eye bearing surface 111 having a curved shape for matingly bearing on the outer surface of the eye (illustrated by dotted line E) and an aperture 112 provided in the plate 110 for allowing a needle 133 of the syringe 130 to pass through the plate 110.

The support 120 comprises a hollow body 121 extending over the aperture 112. The hollow body 121 comprises an inner guiding channel 122. The inner guiding channel 122 extends between a first open end 123 opening onto the aperture 112 and a second open end 124 for introduction of the syringe 130 into the channel 122.

The inner guiding channel 122 is of cylindrical shape and is adapted for receiving a barrel 131 of the syringe 130 in such a way that the syringe can slide into the guiding channel 122 for guiding the needle 133 into the eye. The guiding channel 122 has an inner diameter which corresponds to the outer diameter of the syringe barrel, so that the syringe 130 is guided into the support 120.

The guiding channel 122 is configured such that the syringe can slide relative to the support 120 according to a predefined sliding direction S, which is inclined relative to a radial direction of the eye. More precisely, the guiding channel 122 is arranged so that the needle 133 of the syringe 130 penetrates through the plate 110 with an angle β comprised between 0° and 20°, preferably between 10° and 20°, relative to a radial direction of the bearing surface 111.

Each resilient member 140 comprises a flexible leg 141 projecting from the bearing surface 111 of the plate 110. Each flexible leg 141 has a first end 143 (or connecting end) connected to the plate 110 and a second end 144 (or free end) extending at a distance from the plate 110.

In this first embodiment, the flexible legs 141 are arranged with their connecting ends 143 located at radially opposed positions on the plate 110. Moreover, the flexible legs 141 are oriented with their free ends 144 pointing towards each other in opposite directions, i.e. the legs 141 are directed towards the centre of the plate 110.

Moreover, when the apparatus 100 is at rest (i.e. not in operation), each leg 141 is oriented with an angle a relative to the bearing surface 111.

More precisely, each leg 141 has an elongate shape defining a longitudinal direction, the longitudinal direction of the leg defining an angle a relative to the bearing surface 111 at the connecting end 143 of the leg. The angle a is comprised between 10° and 80°, and is preferably around 45°.

One of the flexible leg 141 has a hole 145 for allowing the needle 133 of the syringe 130 to pass through the flexible leg 141.

Figure 1C:
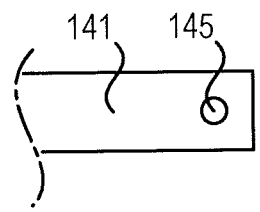
FIGS. 1C and 1D are detailed views of a flexible leg of the apparatus of FIGS. 1A and 1B, FIGS. 2 to 5 illustrate different steps of a method for performing intra-ocular injection using the apparatus of FIGS. 1A and 1B, FIGS. 6A to 6C are respectively schematic front view, detailed view, and side view of an apparatus for intraocular injection according to a second embodiment of the invention

FIG. 1C is an enlarged view of a leg 141 having a hole 145.

Figure 1D:
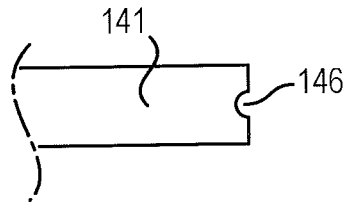
Figure 2:
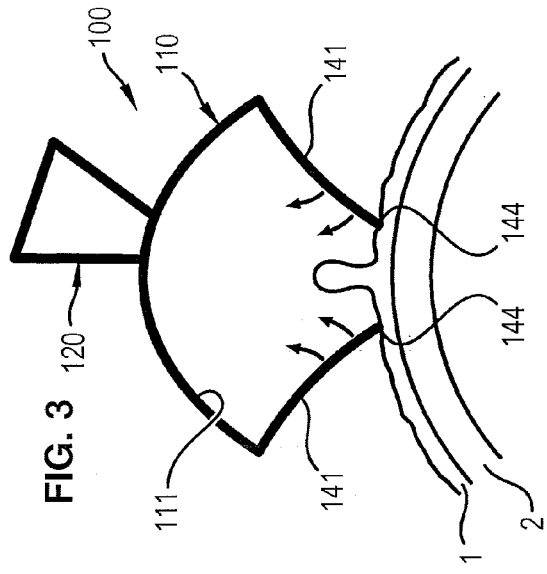
Figure 3:
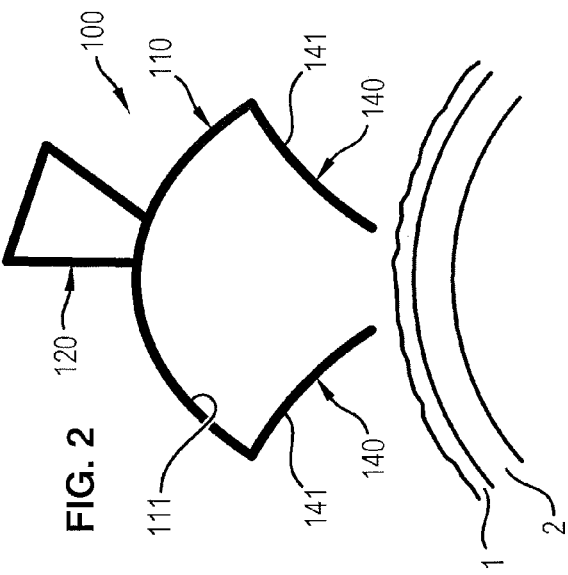
Figure 4:
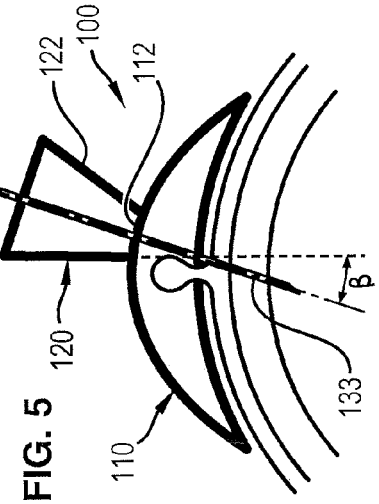
Figure 5:
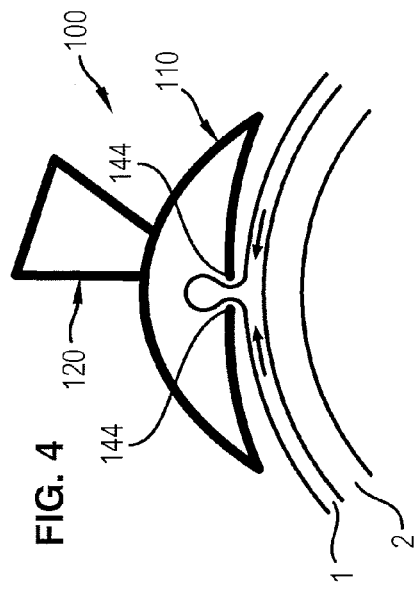

FIG. 1D is an enlarged view of a leg 141 having an encroachment 146 instead of a hole for allowing the needle of the syringe to pass through the flexible leg.

FIGS. 2 to 5 illustrate different steps of a method for performing intra-ocular injection using the apparatus of FIGS. 1A and 1B.

According to a first step (FIG. 2), the operator brings the apparatus 100 into contact with an eye. During this step, the resilient legs 141 come first into contact with the eye.

According to a second step (FIG. 3), while the apparatus 100 is moved toward the eye, the flexible legs 141 are urged against the conjunctival layer 1.

The free ends 144 of the flexible legs 141 engage the conjunctival layer 1 of the eye extending over the scleral layer 2. The free ends 144 engage the conjunctival layer 1 in a zone where the conjunctival layer 1 is mobile relative to the scleral layer 2 (i.e. beyond the limbus).

Due to their resilient character, the legs 141 are bent and their free ends 144 apply opposite tangential forces to the conjunctival layer 1. As result, the conjunctival layer 1 is pinched between the free ends 144 of the resilient legs 141.

Under the pinching action of the flexible legs 141, the conjunctival layer 1 is displaced with respect to scleral layer 2 and forms a fold between the two flexible legs 141.

As the flexible legs 141 apply opposite tangential forces to the conjunctival layer 1, the eye is prevented from moving during the intervention and the conjunctival layer 1 undergoes limited elastic stretching.

According to a third step (FIG. 4), the operator brings the plate 110 into contact with the superficial layer 1, in a position such that the aperture 112 is situated at a distance comprised between 3 and 4 millimeters, preferably of about 3.5 millimeters, from the limbus of the eye.

The operator applies a pressure on the syringe 130 such that the syringe slides into the guiding channel 122 from a retracted position to an injection position in which the needle 133 protrudes out of the body 122 through the aperture 112.

Due to specific configuration of the guiding channel 122, the needle penetrates through the conjunctival layer 1 at the foot of the fold, where the displacement of the conjunctival layer is maximal.

Moreover, the needle penetrates through the conjunctival layer 1 with an angle β comprised between 0° and 20°, preferably between 10° and 20°, relative to a radial direction of the eye at a penetration point.

When the apparatus 100 is removed from the eye, the conjunctival layer 1 slides over the scleral layer 2 back to its initial position. The orifice created in the conjunctival layer 1 by the needle is shifted relative to the orifice created in the scleral layer 2.

Figure 6A:
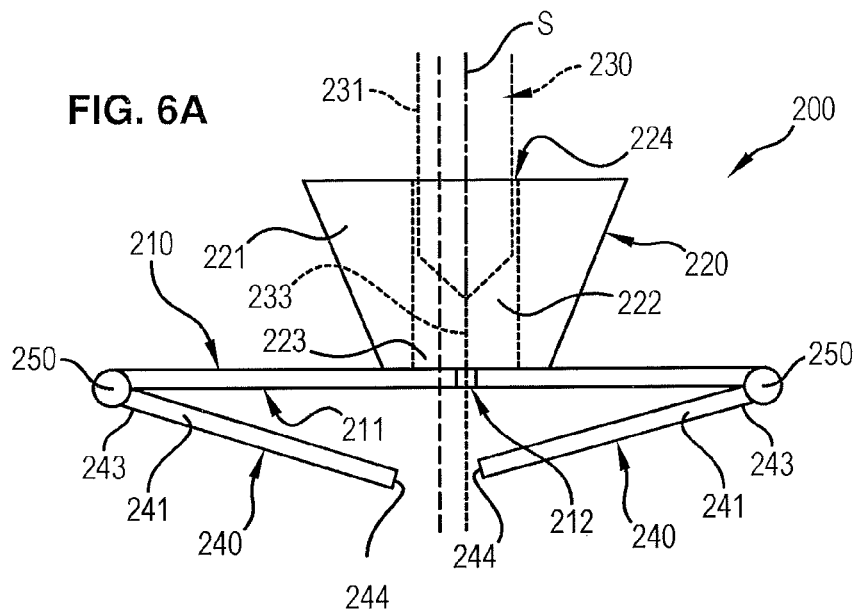
Figure 6B:
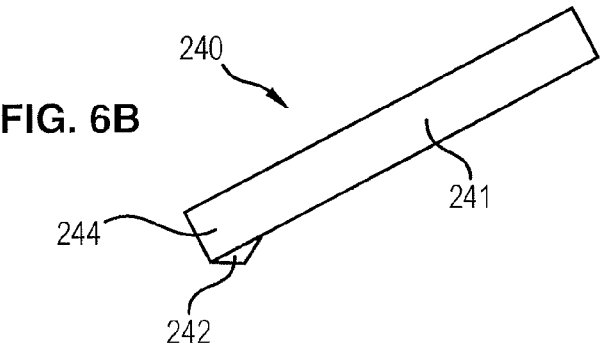
Figure 6C:
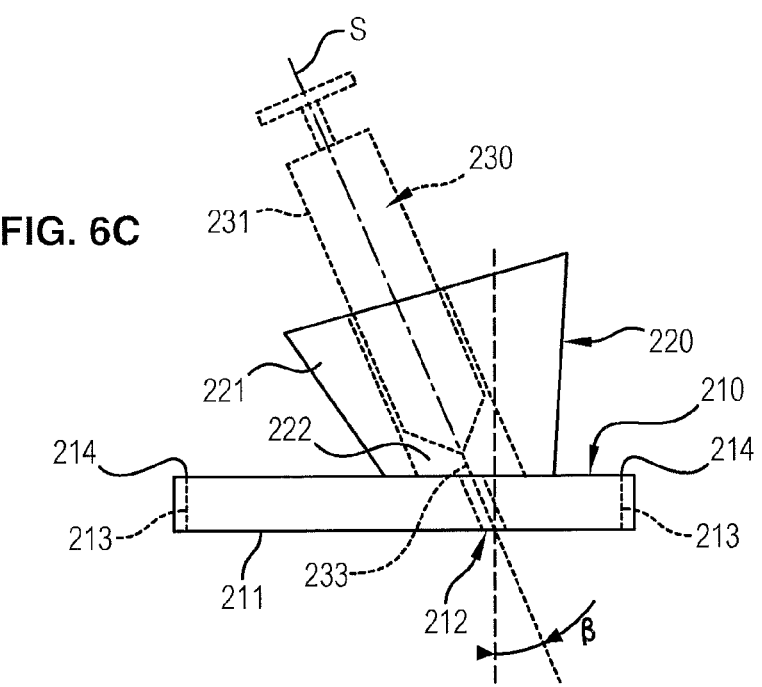

FIGS. 6A to 6C illustrate an apparatus 200 for intraocular injection according to a second embodiment of the invention.

The apparatus 200 comprises a plate 210 adapted for being brought into contact with an eye, a support 220 for receiving a syringe, optionally a syringe 230, and two mobile members 240 for displacing a conjunctival layer of the eye over an underlying scleral layer of the eye.

In this second embodiment, the plate 210 has an eye bearing surface 211 having a flat shape and an aperture 212 provided in the plate 210 for allowing a needle 233 to pass through the plate 210.

Moreover, the plate 210 has two cuts-outs 213, each cut-out 213 having an edge 214 with a curved shape. More precisely, the edge 214 of each cut-out has a substantially circular shape which corresponds to a shape of the limbus so that the edge can be superimposed on the limbus. Each cut-out 213 has a diameter of about 12 millimeters.

The cuts-outs 213 serve as a reference for precisely positioning the apparatus 200 with respect to the eye in order to perform an intra-ocular injection. The cuts-outs 213 are provided in the plate 211, such that when one cut-out is superimposed on the limbus, the aperture 212 is located at a distance comprised between 3 and 4 millimeters, preferably of about 3.5 millimeters from the limbus.

The support 220 comprises a hollow body 221 extending over the aperture 212. The hollow body 221 comprises an inner guiding channel 222. The inner guiding channel 222 extends between a first open end 223 opening onto the aperture 212 and a second open end 224 for introduction of the syringe 230 into the channel 222.

The inner guiding channel 222 is of cylindrical shape and is adapted for receiving a barrel 231 of the syringe 230 in such a way that the syringe can slide into the guiding channel 222 for guiding the needle 233 through the eye. The guiding channel 222 has an inner diameter which corresponds to the outer diameter of the syringe barrel, so that the syringe 230 is guided into the support 220.

The guiding channel 222 is configured such that the syringe 230 can slide relative to the support 220 according to a predefined sliding direction S, which is inclined relative to a radial direction of the eye.

Each mobile member 240 comprises a pivoting leg 241 projecting from the bearing surface 211. Each pivoting leg 241 has a first end 243 (or connecting end) connected to the plate 110 though a respective hinge 250 and a second end 244 (or free end) extending at a distance from the plate. The hinges 250 allow free rotation of the legs with respect to the plate 210.

In this second embodiment, the pivoting legs 241 are arranged with their connecting ends 243 located at radially opposed positions on the plate 210. Moreover, the pivoting legs 241 are oriented with their free ends 144 pointing towards each other, i.e. the legs 141 are directed towards the centre of the plate 110.

As illustrated on FIG. 6B, each mobile member 240 also comprise a protrusion 242 (or teeth) arranged at the free end 244 of the pivoting leg 241 for engaging the superficial layer of the eye. The protrusion can have a dimension (or height) of between 0.1 and 0.5 millimeters so as to be able to bite or impale into the conjunctival tissue.

Alternatively, the free ends 244 of the pivoting legs 241 can have hydrophilic properties for providing good adhesion of the free end 244 to the conjunctival layer. Such hydrophilic properties may be obtained through the use of a hydrophilic material for making the legs, by subjecting the legs to a surface treatment (chemical grafting or plasma) or a mechanical treatment for enhancing rugosity, or by coating the legs with a specific porous or fibrous material.

As illustrated on FIG. 6C, the guiding channel 222 is configured such that the syringe can slide relative to the support 220 according to a predefined sliding direction S, which is inclined relative to a radial direction of the eye. More precisely, the guiding channel 222 is arranged so that the needle of the syringe penetrates through the plate 210 with an angle β comprised between 0° and 20°, preferably between 10° and 20°, relative to a direction perpendicular to the plate 210.

Thus, in operation, the needle penetrates through the conjunctival layer with an angle comprised between 0° and 20°, preferably between 10° and 20°, relative to a radial direction of the eye at a penetration point. This avoids touching the lens and allows to increase path length into the thickness of the scleral layer so as to limit drug reflux.

The apparatus 200 can be operated in the same way as the apparatus 100 (FIGS. 2 to 5).

The needle is inserted through the eye tissues, with a penetration length varying from 0.1-1.0 millimeter (suprachoroidal space injection) to 2-13 millimeters for intravitreal injection (injection inside the vitreous or center of the globe).

The composition can be injected manually using a standard hypodermic syringe, an injection device as disclosed in document WO 2008/084064, or an injection device as disclosed in document U.S. Pat. No. 7,678,078.

The apparatus can be used as an accessory to injection devices as disclosed in documents WO 2008/084064 or U.S.

Pat. No. 7,678,078. In such case, the apparatus including the plate, the mobile legs and the support can be equipped with a handle.

Figure 7C:
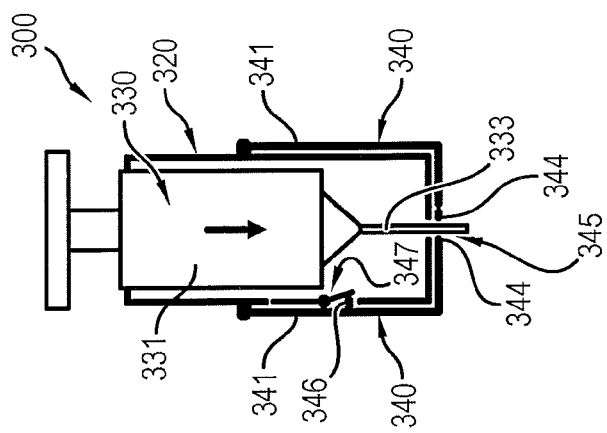
FIGS. 7A to 7C are schematic views of an apparatus for intraocular injection according to a third embodiment of the invention.
Figure 7B:
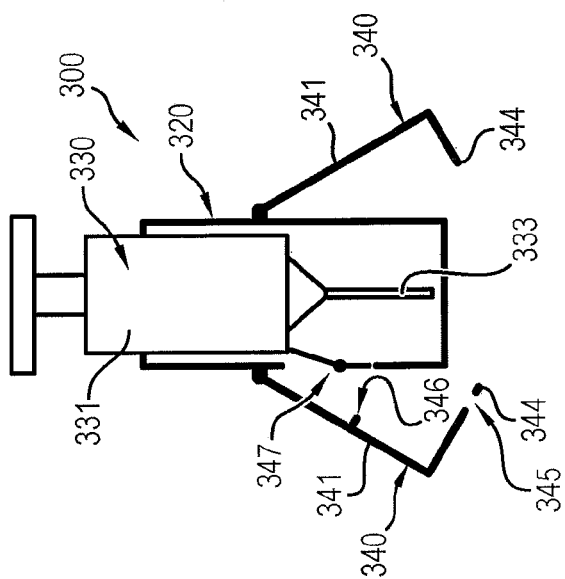
Figure 7A:
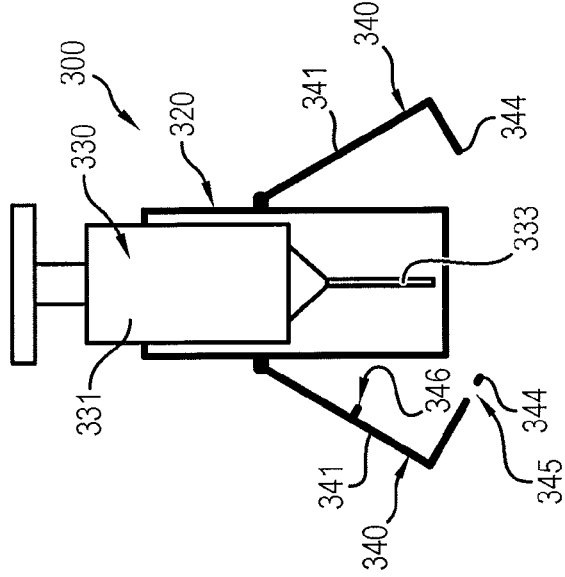

FIG. 7A is a schematic view of an apparatus 300 for intraocular injection according to a third embodiment of the invention.

The apparatus 300 comprises a support 320 for receiving a syringe, optionally a syringe 330, and two mobile members 340 for displacing a conjunctival layer of the eye over an scleral layer of the eye.

The apparatus 300 is operated manually, as a plier, with the two mobiles members 340 forming two jaws for pinching the conjunctive layer.

Each mobile member 340 (or jaws) comprises a pivoting member 341 having a first end 343 (or connecting end) hinged to the support 320 and a second end 344 (or free end) extending at a distance from the plate.

The pivoting legs 341 are L-shaped or curved and oriented with their free ends 344 pointing towards each other.

The mobile members 340 can be manually pressed together so as to be brought closer one to the other for pinching the conjunctival layer so as to form a fold in the conjunctival layer, without applying pressure on the eye.

The apparatus comprises releasable locking means for preventing movement of the syringe or activation of the injection device relative to the support until the fold is formed. One of the mobile members 340 comprises means 346 for unlocking the injection device when the mobile member 340 is brought sufficiently closed to the other mobile member.

Such an apparatus 300 ensures that activation of the injection device is possible only after an appropriate fold has been formed in the conjunctival layer.

In such an apparatus, the support 320 and the mobile members are arranged so that the needle 333 penetrates through the conjunctival layer of the eye at the foot of the fold.

A shown on FIGS. 7B and 7C, the releasable locking means comprises a mobile finger 347. The finger 347 is mobile relative to the support 320 between a locked position (FIG. 7B), wherein the finger protrude within the guiding channel 322 of the support 320 and a release position (FIG. 7C), wherein the finger 347 is retracted.

When the finger 347 is in the locked position, the barrel 331 of the syringe 330 abuts against the finger, thereby preventing axial movement of the syringe 330. When the finger 347 is retracted, the barrel 331 is free to slide within the guiding channel 322.

When the leg 341 is brought closer to the support 320, the leg 341 causes the finger 347 to pivot from the locked position to the released position.

Figure 8:
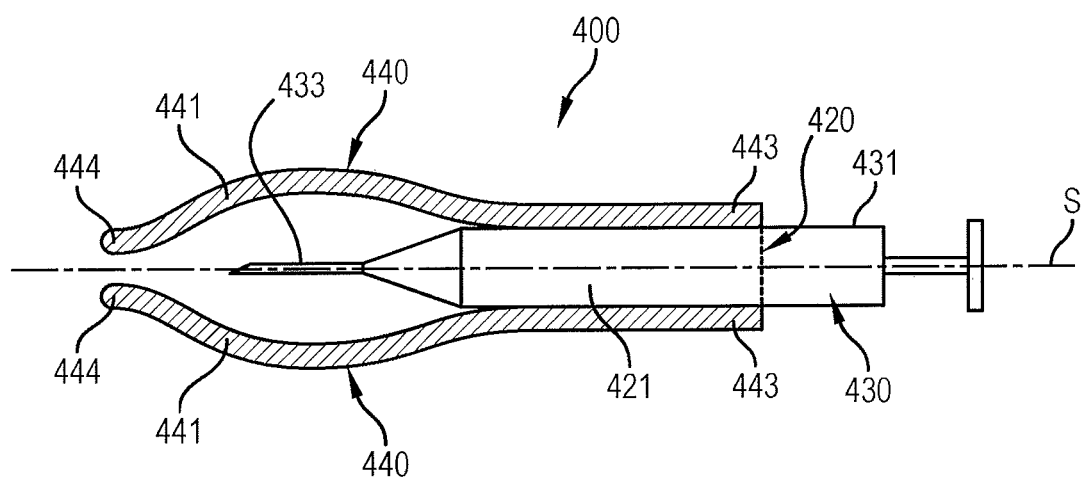
FIG. 8 is a schematic view of an apparatus for subconjunctival or subtenon injection according to a fourth embodiment of the invention.

FIG. 8 is a schematic view of an apparatus 400 for subconjunctival or subtenon injection according to a fourth embodiment of the invention.

The apparatus 400 comprises a support 420 for receiving a syringe, optionally a syringe 430, and two mobile members 440 for displacing a conjunctival layer of the eye over an underlying scleral layer of the eye.

The apparatus 400 is operated manually, as a plier, with the two mobiles members 440 forming two jaws for pinching the conjunctival layer.

The support 420 comprises a hollow body 421 for accommodating and guiding the syringe 430.

The hollow body 241 is configured such that the syringe 430 can slide relative to the support 420 according to a predefined sliding direction S, which is parallel to a tangential direction of the eye.

Each mobile member 440 (or jaw) comprises a pivoting leg 441 projecting from the support 420. Each leg 441 has a first end 443 (or connecting end) connected to the support 420 and a second end 444 (or free end) extending at a distance from the support 420.

The legs 441 have an elongate shape and are arranged on both sides of the support 420 with their longitudinal direction substantially parallel to the direction of sliding of the syringe (direction of injection). However, the legs 441 have a slightly curved shape with their free ends 444 pointing towards each other.

FIGS. 9 to 11 illustrate different steps of a method for performing subconjunctival injection using the apparatus 400 of FIG. 8.

According to a first step (FIGS. 9A and 9B), the operator brings the apparatus 400 into contact with an eye. More precisely, the operator brings the free ends 444 of the legs 441 into contact with the conjunctival layer of the eye.

According to a second step (FIGS. 10A and 10B), the mobile members 440 are pressed together so as to be brought closer one to the other for pinching the conjunctival layer.

Under the pinching action of the legs 441, the conjunctival layer 1 is displaced with respect to the scleral layer 2 and forms a fold between the two legs 441.

As the flexible legs 441 apply opposite tangential forces to the conjunctival layer 1, the eye globe is prevented from moving during the intervention and the conjunctival layer undergoes limited elastic stretching.

According to a third step (FIGS. 11A and 11B), the operator applies a pressure on the syringe 430 such that the syringe slides into the support 420 from a retracted position to an injection position in which the needle 433 is brought slightly over the two free ends 444 of the legs 441.

The needle 433 is moved according to a direction parallel to a tangential direction of the eye, and the tip of the needle 433 penetrates at the fold, just between the conjunctival layer 1 and the underlying scleral layer 2.

The operator keeps applying a pressure on the syringe 430, so as composition is injected between the conjunctival layer 1 and the scleral layer 2.

When pressure is released on the mobile members 440, the mobile members are moved apart from each other, back to their initial position (FIGS. 9A and 9B).

The conjunctival layer 1 slides over the scleral layer 2, back to its initial position.

Such an apparatus 400 allows injection of the composition between the conjunctival layer and the scleral layer, by taking advantage of the fold formed in the conjunctival layer by the mobile members 440, hence avoiding accidental intraocular injection.

An advantage of the apparatus 300 and 400 according to third and second embodiments is that the mobile members can be brought closer to each other, without needing to press the apparatus in a radial direction against the eye globe. This avoids sinking of the eye globe into the eye-socket during operation and allows better control of the positioning of the apparatus relative to the eye globe.

The invention claimed is:

1. An apparatus for injection into an eye comprising:
    two mobile legs projecting from a support surface, where the two mobile legs are configured to each move towards each other when the support surface is moved toward an outer surface of the eye causing the two mobile legs to engage a conjunctival layer of the eye over an underlying scleral layer of the eye and to pinch the conjunctival layer creating a fold in the conjunctival layer, and
    a guiding channel connected to the support surface and configured to guide a needle through the conjunctival layer once the fold has been formed.

2. The apparatus according to claim 1, wherein the guiding channel comprises a hollow body adapted for receiving a barrel of a syringe.

3. The apparatus according to claim 1, wherein the guiding channel is arranged so that the needle penetrates through the conjunctival layer at a foot of the fold.

4. The apparatus according to claim 1, wherein the guiding channel is arranged so that the needle penetrates through the conjunctival layer at the fold for injection between the conjunctival layer and the scleral layer.

5. The apparatus according to claim 1, wherein the guiding channel is arranged so that the needle penetrates through the conjunctival layer with an angle comprised between 0° and 20°, preferably between 10° and 20°, relative to a radial direction of the eye at a penetration point.

6. The apparatus according to claim 1, wherein the guiding channel is arranged so that the needle penetrates through the conjunctival layer according to a direction parallel to a tangential direction of the eye at the fold.

7. The apparatus according to claim 1, comprises a releasable lock configured to prevent accidental movement of the needle relative to the guiding channel before the fold is formed.

8. The apparatus according to claim 1, further comprises a needle release configured to release the needle once the fold is formed.

9. The apparatus according to claim 1, wherein one of the mobile legs comprises a hole or an encroachment for allowing the needle to pass through the mobile leg.

10. The apparatus according to claim 9, comprising a plate for being brought into contact with the eye.

11. The apparatus according to claim 10, wherein the mobile legs are extending from the plate, the mobile legs being caused to flex relative to the plate when the plate is brought close to the eye.

12. The apparatus according to claim 10, wherein each mobile leg is arranged so as to form an angle comprised between 10° and 80° relative to a bearing surface of the plate.

13. The apparatus according to claim 10, wherein the plate comprises a cut-out having an edge adapted to be positioned along a limbus delimiting a cornea and a scleral of the eye so as to adjust a position of the guiding channel relative to the limbus.

14. The apparatus according to claim 13, wherein the two mobile legs comprise free ends adapted for biting into the conjunctival layer.

* * * * *